(12) United States Patent
Hendrick

(10) Patent No.: US 9,345,508 B2
(45) Date of Patent: May 24, 2016

(54) MATERIAL CAPTURING GUIDEWIRE

(71) Applicant: The Spectranetics Corporation, Colorado Springs, CO (US)

(72) Inventor: Brandon Thomas Hendrick, Colorado Springs, CO (US)

(73) Assignee: The Spectranetics Corporation, Colorado Springs, CO (US)

( * ) Notice: Subject to any disclaimer, the term of this patent is extended or adjusted under 35 U.S.C. 154(b) by 0 days.

(21) Appl. No.: 14/686,424

(22) Filed: Apr. 14, 2015

(65) Prior Publication Data

US 2015/0216547 A1 Aug. 6, 2015

Related U.S. Application Data

(62) Division of application No. 13/801,149, filed on Mar. 13, 2013, now abandoned.

(51) Int. Cl.
| | | |
|---|---|---|
| A61B 17/22 | (2006.01) | |
| A61B 17/3207 | (2006.01) | |
| A61B 18/24 | (2006.01) | |
| A61B 17/3205 | (2006.01) | |
| A61B 17/32 | (2006.01) | |

(52) U.S. Cl.
CPC ........... *A61B 17/3207* (2013.01); *A61B 18/245* (2013.01); *A61B 17/32053* (2013.01); *A61B 2017/22034* (2013.01); *A61B 2017/22042* (2013.01); *A61B 2017/320064* (2013.01); *A61B 2017/320716* (2013.01)

(58) Field of Classification Search
CPC .................... A61B 17/32053; A61B 17/3207; A61B 17/50; A61B 2017/22034; A61B 2017/22042; A61B 2017/320056; A61B 2017/320064; A61B 18/245
USPC ............................ 606/159, 127; 604/508, 22
See application file for complete search history.

(56) References Cited

U.S. PATENT DOCUMENTS

| | | | |
|---|---|---|---|
| 4,790,310 A * | 12/1988 | Ginsburg | A61B 18/245 219/121.8 |
| 5,009,659 A | 4/1991 | Hamlin et al. | |
| 5,078,723 A * | 1/1992 | Dance | A61B 17/3207 604/22 |
| 5,643,251 A | 7/1997 | Hillsman et al. | |
| 5,697,944 A | 12/1997 | Lary | |
| 7,008,434 B2 | 3/2006 | Kurz et al. | |
| 7,780,650 B2 | 8/2010 | Frassica et al. | |
| 2004/0199191 A1 | 10/2004 | Schwartz | |
| 2007/0265648 A1 | 11/2007 | Cohen | |
| 2009/0018565 A1* | 1/2009 | To | A61B 17/320758 606/159 |
| 2010/0030247 A1 | 2/2010 | Pikus et al. | |
| 2011/0251629 A1 | 10/2011 | Galdonik et al. | |

* cited by examiner

*Primary Examiner* — Todd E Manahan
*Assistant Examiner* — Erich Herbermann
(74) *Attorney, Agent, or Firm* — Faegre Baker Daniels LLP

(57) ABSTRACT

This disclosure discusses various methods and devices for capturing plaque that is to be removed from a blood vessel after the plaque has been separated from the blood vessel or remaining plaque.

9 Claims, 4 Drawing Sheets

MATERIAL CAPTURING GUIDEWIRE

CROSS REFERENCE TO RELATED APPLICATION

The present application is a divisional of prior U.S. application Ser. No. 13/801,149 filed Mar. 13, 2013, entitled Material Capturing Guidewire, which is hereby incorporated herein by reference in its entirety for all that it teaches and for all purposes.

FIELD OF THE DISCLOSURE

The present disclosure relates generally to guidewires, including methods for using guidewires and systems incorporating guidewires for capturing and removing unwanted plaque in a patient's vascular system.

BACKGROUND

Peripheral arterial disease (PAD) is a disease in which plaque builds up in the arteries that carry blood to a subject's head, organs, and limbs. Plaque is made up of fat, cholesterol, calcium, fibrous tissue, and other substances in the blood. Over time, plaque hardens and narrows the subject's arteries. This limits the flow of oxygen-rich blood to the subject's organs and other parts of the body. When plaque builds up in the body's arteries, the condition is called atherosclerosis. Atherosclerosis (also known as arteriosclerotic vascular disease or ASVD) is a condition in which an artery wall thickens. This condition is commonly referred to as a hardening or furring of the arteries.

Atherosclerosis can affect any artery in the patient's vascular system, including arteries in the heart, brain, arms, legs, pelvis, and kidneys. As a result, diseases other than PAD, may develop based on which arteries are affected. For example, coronary heart disease (CHD), also called coronary artery disease occurs when plaque builds up in the coronary arteries, thereby narrowing the coronary arteries and reducing blood flow to the heart muscle. If blood flow to the heart is reduced or blocked, the subject may incur chest pain or discomfort or a heart attack. Carotid artery disease occurs if plaque builds up in the arteries on each side of a subject's neck (the carotid arteries), which supply oxygen-rich blood to the brain. If blood flow to the brain is reduced or blocked, the subject may have a stroke. Chronic kidney disease can occur if plaque builds up in the renal arteries, which supply oxygen-rich blood to the kidneys. Accordingly, chronic kidney disease may cause a gradual loss of kidney function.

A variety of options, including surgery, exist for treating atherosclerosis. One such surgical option is atherectomy, which is a minimally invasive surgical procedure for removing plaque from the blood vessel (e.g., artery, vein, vein graft) with a catheter. The catheter generally has a working tip, such as a sharp blade to cut the plaque or a laser to ablate the plaque. These catheters, particularly, the sharp bladed catheter, may also be designed to collect the cut plaque in a chamber its tip, thereby allowing the plaque to be removed as the device is removed from the blood vessel. Examples of such mechanical cutting atherectomy catheters may include those illustrated and discussed in U.S. Publication Nos. 2008/0154293 and 2008/0154296 both of which are incorporated herein by this reference in their entirety.

Additionally, examples of laser ablation atherectomy catheters may include in U.S. Pat. Nos. 5,456,680 and 5,643,251 both of which are incorporated herein by this reference in their entirety. Furthermore, Spectranetics Corporation, the assignee of this disclosure, sells a coronary laser atherectomy catheter under the trade name ELCA™ and a laser ablation under the trade name Turbo Elite™, which is used to treat PAD, particularly above and below the knee. Laser catheters, such as these, have a plurality of laser emitters at its distal tip. The catheters may also have a central passageway or lumen which receives a guidewire. The guidewire is typically inserted into the blood vessel prior to catheter introduction and traverses the occlusion. Once the guidewire is inserted, it facilitates the advancement and placement of the catheter to the selected portion(s) of the blood vessel for laser ablation of plaque.

SUMMARY

Accordingly, there is a need for a device, method and/or system such as a guidewire that has the ability not only to traverse the plaque or other lesion material, but also to engage, within a blood vessel, the plaque or other lesion material that is to be removed.

A method for removing plaque within a blood vessel, according to this disclosure, may include the steps of inserting a guidewire into a blood vessel, attaching plaque within the blood vessel to a portion of the guidewire, inserting a catheter into the blood vessel over the guidewire, separating at least a portion of the plaque from the blood vessel using the catheter, and concurrently removing, from the blood vessel, the guidewire and the plaque attached to the guidewire.

A device, according to this disclosure, for performing the method may include a guidewire for insertion into a blood vessel having an elongated member and a roughened (e.g., irregular, abrasive, or otherwise contoured) surface on the elongated member configured to attach plaque within a blood vessel to the elongated member.

A device, according to this disclosure, for performing such method, may also include a guidewire having an elongated member, and a means for attaching plaque within a blood vessel to the elongated member.

The roughened surface and/or means for attaching the plaque to the elongated member may include a plurality of protrusions, such as tines or barbs, extending radially from the elongated member, thereby providing the plaque the type of structure onto which the plaque can attach. Alternatively the roughened surface and/or means for attaching the plaque to the elongated member may include a flute within the guidewire. These means may also provide the clinician, who is navigating the guidewire through the subject's blood vessel, tactile feedback when a portion of the guidewire has reached, traversed or engaged the plaque at the lesion site.

The guidewire can further include an unroughened surface on the elongated member having a degree of roughness less than that of the roughened surface. Commonly, the unroughened surface is at a proximal portion of the guidewire, and the roughened surface is at a distal portion of the guidewire. Surface roughness measurement(s) can be done using surface measurement or metrology techniques. As will be appreciated, surface measurement determines surface topography. Surface measurement conceptually includes surface shape, surface finish, surface profile roughness ($R_a$), or in surface area roughness ($S_a$), surface texture, asperity and structural characterization. In three dimensional optical profilometry, roughness is usually expressed as surface area roughness (Sa). Profile roughness (Ra) can be extracted as a line through an area. Interestingly, Sa is also able to report average Ra through a surface by averaging several profiles.

The guidewire's engagement of the plaque assists in the plaque attaching to the guidewire and remaining attached to the guidewire while a separation device, such as a mechanical cutting or laser ablation catheter, separates the plaque or other lesion material from the blood vessel. Because the plaque or other lesion material remains captured and attached to the guidewire, once the plaque is separated from the blood vessel, the plaque can be removed from the blood vessel as a substantially solid object along with removal of the guidewire. In other words, the separated plaque may be able to be completely removed from the blood vessel along with the guidewire through a lumen within the catheter and/or along with the catheter, thereby potentially reducing the possibility that particles of plaque may be left behind in the blood vessel when the catheter is removed.

Similarly, the guidewire may be inserted into the separation device after the plaque or other lesion material has been separated from the blood vessel. Upon being inserted into the separation device, the guidewire may engage the separated plaque within the separation device and be removed from the separation device as a substantially solid object.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" may be used interchangeably herein. It is also to be noted that the terms "comprising", "including", and "having" may be used interchangeably.

A "barb" is a projection having a relatively dull or sharp point facing in a direction opposite to that in which the device to which it is attached initially travels. Examples of objects that have a barb include an arrow, a harpoon and a fish hook.

A "catheter" is a tube that can be inserted into a body cavity, duct, lumen, or blood vessel, such as the vasculature system. In most uses, a catheter is a relatively thin, flexible tube ("soft" catheter), though in some uses, it may be a larger, solid, less flexible—but possibly still flexible—catheter ("hard" catheter). Additionally, the catheter may also have a working tip, such as a sharp blade to cut the bodily material (e.g., plaque) or a laser to ablate the bodily material, with which it contacts.

A "flute" is a groove that may twist around the elongated member in which it is formed. Flutes can vary in size and shape. Additionally, the number of flutes may also vary. An example of a device that includes a flute is a drill bit, which typically has a one or more relatively deep grooves that twist around the bit.

The term "means" as used herein shall be given its broadest possible interpretation in accordance with 35 U.S.C., Section 112, Paragraph 6. Accordingly, a claim incorporating the term "means" shall cover all structures, materials, or acts set forth herein, and all of the equivalents thereof. Further, the structures, materials or acts and the equivalents thereof shall include all those described in the summary of the invention, brief description of the drawings, detailed description, abstract, and claims themselves.

The term "plaque" shall mean material within a subject's vascular system that comprises fat, cholesterol, calcium, fibrous tissue, and other substances in the blood.

The term "roughened" refers to a surface that is uneven, irregular, coarse, rough, not smooth, abrasive, and/or unlevel. For example, a roughened surface can be a surface marked by irregularities, protuberances, projections, inequalities, and/or ridges.

A "tine" is a branching spike or prong or other type of protrusion configured to engage bodily material, including plaque. Tines may be blunt or sharp, and tines may be constructed of biocompatible material.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure may be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

DETAILED DESCRIPTION

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Figure 1:
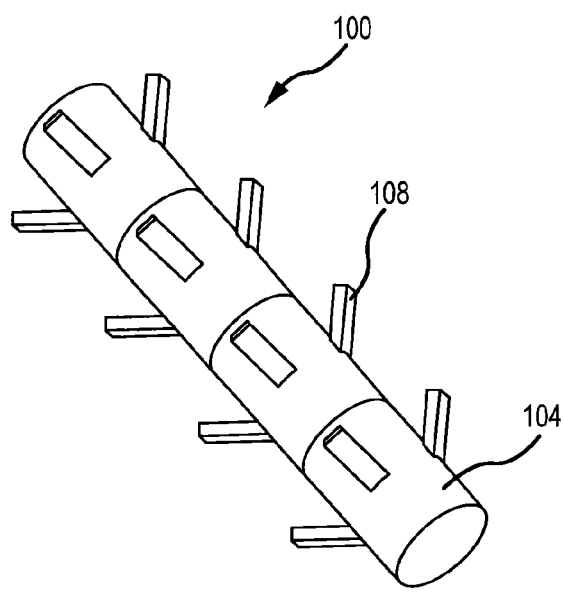
FIG. 1 is a perspective view of an embodiment of a portion of a guidewire having a plurality of tines extending therefrom.

With reference to FIG. 1, a portion of an exemplary guidewire 100 is depicted. The guidewire 100 includes an elongated member 104 and a plurality of tines 108 protruding radially therefrom. The guidewire 100, including both the elongated member 104 and tines 108, may be constructed as a solid object. Alternatively, the elongated member 104 and tines 108 may be formed separately and combined, such as attaching the tines 108 to the elongated member 104. The guidewire 100 may preferably be constructed of a rigid and flexible biocompatible material, such as stainless steel or biocompatible polymers. Additionally, the elongated member 104 itself may be a solid object, such as a wire, or a braided object or wire, or other type of non-elastic construction. If the tines 108 are constructed separately, then they may also be constructed of the same or different materials and/or constructions used form the elongated member.

As will become evident in the discussion of FIGS. 2A-2D, the size, length and configuration of the guidewire 100, including the elongated member 104 and tines 108, may vary. For example, the tines 108 may protrude from the elongated member 104 in a direction toward the proximal end of the guidewire 100, in a direction toward the distal end of the guidewire 100, or in a radial direction that is directed neither toward either distal end. Those skilled in the art will appreciate that there are numerous other sizes, lengths and configurations of the guidewire, and all such sizes, lengths and configurations within the knowledge of one skilled in the art are considered within the scope of this disclosure.

Figure 2A:
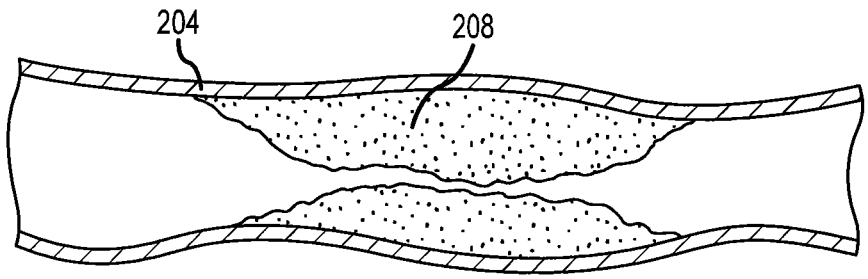
FIG. 2A is a cross-sectional view of a blood vessel having plaque therein.
Figure 2B:
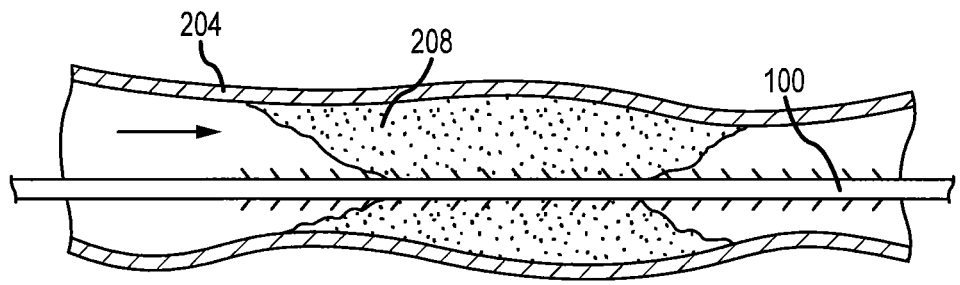
FIG. 2B is a cross-sectional view of the blood vessel of FIG. 2A with the guidewire of FIG. 1 traversing and engaging the plaque.

With reference to FIG. 2A through 2D, there is depicted the guidewire 100 used to remove a substantially solid portion 216 of plaque from a blood vessel 204 after a catheter 212 has separated the plaque 208 from the blood vessel 204. Specifically, referring to FIG. 2A, there is a shown a blood vessel 204 having plaque 208 attached to its interior wall(s). Referring to FIG. 2B, the guidewire 100 is inserted into the blood vessel 204 in a direction illustrated by the arrow (→). As and/or after the guidewire traverses the plaque 208 in the indicated direction (→), the tines engage the plaque 208, and the plaque 208 attaches to the guidewire 100. It may be preferable that the size of the guidewire 100 be of such a sufficient size that its diameter, either with or without the tines, is greater than that of the opening in the plaque and/or space between the plaque and blood vessel. Using a guidewire 100 of this size may further facilitate the engagement of the tines and plaque and may also push the plaque 208 against the blood vessel 204, thereby increasing the density of the object of plaque to be removed from the subject.

Figure 2C:
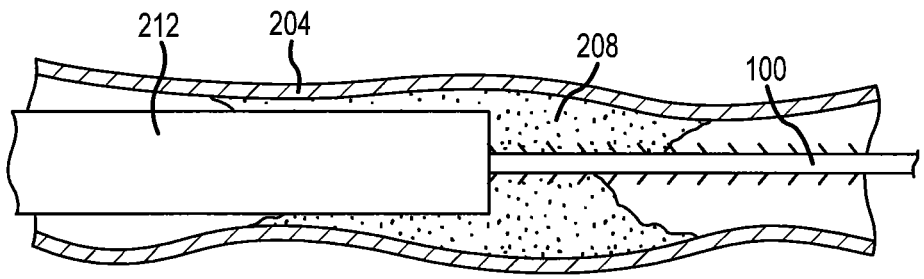
FIG. 2C is a cross-sectional view of the blood vessel and plaque of FIG. 2B with a catheter located over the guidewire of FIG. 1 and separating the plaque from the blood vessel while the plaque remains engaged with the guidewire.
Figure 2D:
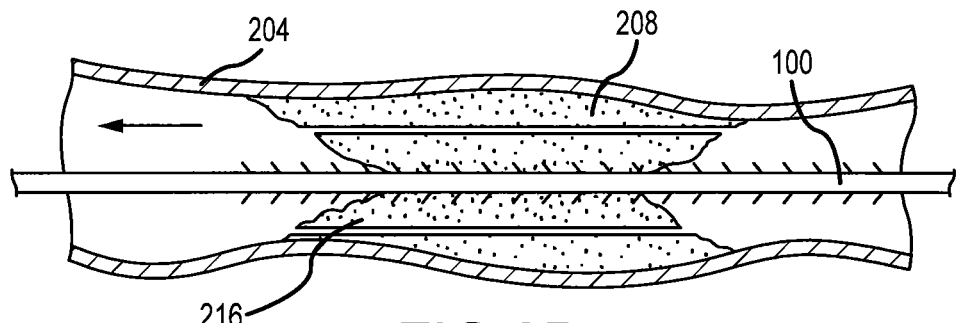
FIG. 2D is a cross-sectional view of the blood vessel of FIG. 2B with the plaque separated from the blood vessel while the plaque remains engaged with the guidewire.

Referring to FIG. 2C, a catheter 212 is located over the guidewire 100. The catheter 212 preferably has a lumen (not shown) into which the guidewire is inserted. As the catheter 212 travels toward and/or beyond the plaque 208, the catheter 212 slides over and travels along the path of the guidewire 100. As discussed above, the catheter generally has a working tip, such as a sharp blade to cut the plaque or a laser to ablate the plaque. Accordingly, as the catheter 212 slides over and travels along the path of the guidewire 100 and reaches the plaque 208, the working tip of the catheter separates the plaque from itself and/or the blood vessel via a coring action. While and upon doing so, a portion 216 of the plaque remains attached to the guidewire 100 in the possible shape of a plug. And when the guidewire 100 is removed from the blood vessel 204 in a direction (←) illustrated in FIG. 2D, so is the object (or plug) 216 of plaque. The object 216 of plaque may be removed from the blood vessel 204 along with the guidewire 100 or prior to or after the guidewire is removed.

Figure 3:
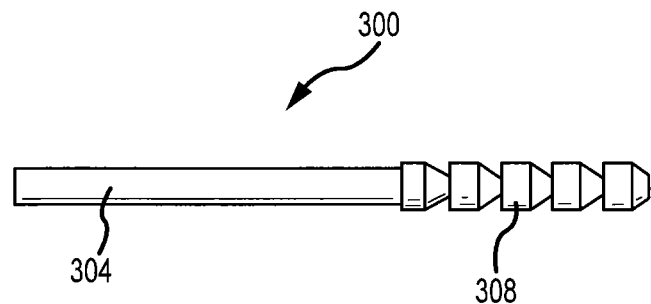
FIG. 3 is an elevation view of an embodiment of a portion of a guidewire having a plurality of barbs.

Although the discussion regarding FIGS. 2A-2D included the use of the guidewire 100 depicted in FIG. 1, those skilled in the art will appreciate that there are numerous other shapes, sizes and configurations of guidewires, as well as other types of means, that may be used to engage plaque and attach it to the guidewire. For example, referring to FIG. 3, a guidewire 300 may have protrusions in the shape of barbs 308—rather than tines—that are attached to or formed integral with the elongated element 304. Additionally, any type of protrusion extending in a generally radial direction that is capable of engaging tissue may be used. Conversely, notches imparted along and within the elongated element that are configured to allow plaque to adhere and attach to the guidewire may be used in lieu of protrusions.

Figure 4:
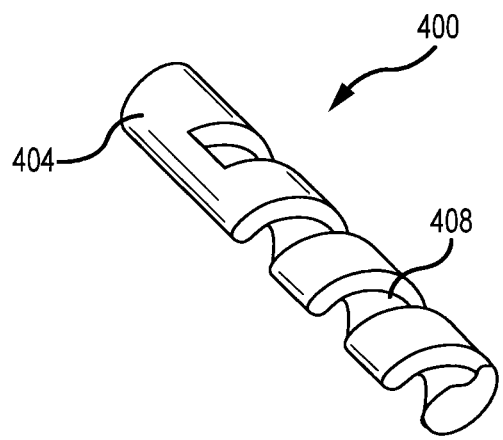
FIG. 4 is a perspective view of an embodiment of a portion of a guidewire having a flute included therein.

With reference to FIG. 4, there is depicted a further alternative means for attaching plaque to a guidewire. This figure illustrates guidewire 400 having a helically shaped flute 408 at the distal end of an elongated element 404. The elongated shaft may preferably be of a sufficient size and configuration such that the diameter of the elongated element 404 and/or the effective inner diameter of the flute is greater than that of the opening in the plaque and/or space between the plaque and blood vessel, thereby facilitating the flute's engagement of the plaque and attachment to the guidewire similar to the way in which a slowly rotating drill bit engages the material into which the bit is being inserted. Although the guidewire 400 depicted in FIG. 4 includes only one flute 408 having a certain helical shape, those skilled in the art will appreciate that the guidewire may include a plurality of flutes and/or the flute(s) may be configured in numerous other sizes, lengths and configurations, and all possible flute sizes, lengths and configurations within the knowledge of one skilled in the art are considered within the scope of this disclosure. For example, the flute 408 of guidewire 400 is located at the distal end portion of the guidewire 400. However, it shall be understood that the flute may be located at a location toward the proximal end portion of the guidewire and/or encompass a larger length of the guidewire, including potentially the entire length of the guidewire.

Figure 5A:
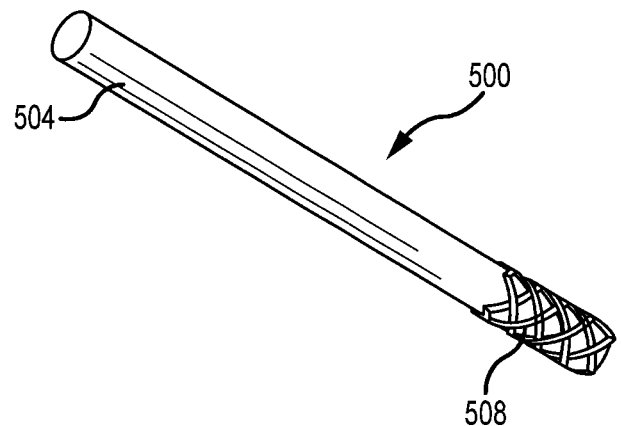
FIG. 5A is a perspective view of an embodiment of a portion of a guidewire comprising an un-deployed braided element.
Figure 5B:
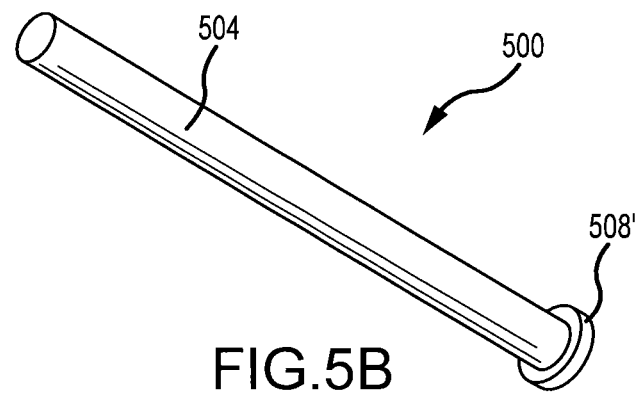
FIG. 5B is a perspective view of an embodiment of a portion of a guidewire comprising a deployed braided element.

With reference to FIGS. 5A and 5B, there is depicted a further alternative means for attaching plaque to a guidewire. These figures illustrate a guidewire 500 having a braided (or mesh-like or coiled-like) element 508 at the distal end of an elongated element 504. Specifically, FIG. 5A illustrates the braided element 508 attached to the periphery of the elongated element 504 at its distal portion in an un-deployed state, and FIG. 5B illustrates the braided element 508 in a deployed state at the distal end of the elongated element 504. As the braid element 508 is deployed, it expands radially into the plaque, as is generally known by one of skill in the art, such as described in U.S. Patent Publication 2001/0000349, which is hereby incorporated by reference. Once the braided element 508 is attached to the plaque, the separated plaque may be removed either alone through the lumen of the separation device and/or in conjunction with the removal of the separation device from the blood vessel.

The braided element may have different sizes, shapes and configuration in either its un-deployed stated or deployed state. Depending upon the configuration of the braided element, particularly in its deployed state, the braided element can also act as a stopper, piston, and/or plunger that can be deployed proximally or distally of the plaque. Once deployed distally of the plaque, the braided element may be used pull the separated plaque proximally within the lumen of the separation device or the blood vessel. And when deployed proximally of the plaque, the braided element may be used to push the separated plaque proximally within the lumen of the separation device or the blood vessel. Additionally, the braided element may be partially or completed deployed to and obtain different configurations. Furthermore, the braided element may be deployed in multiple times within a surgical procedure. For example, the braided element may be deployed and act as a plunger, then retract into an un-deployed state, while located within the blood vessel and/or separation device, and then be re-deployed at a different position with respect to the plaque and act as a piston. Then process can then be repeated and/or performed in reverse order. Such a process may be helpful in dislodging and/or removing plaque or lesion material that is lodged within the blood vessel or separation device. For example, this process may be used to dislodge plaque or lesion material within the catheter described in copending U.S. patent application Ser. No. 13/800,651, filed Mar. 13, 2013, and entitled "System And Method Of Ablative Cutting And Pulsed Vacuum Aspiration", which is incorporated herein by this reference in its entirety.

In the appended figures, similar components and/or features may have the same reference label. Further, various components of the same type may be distinguished by following the reference label by a letter that distinguishes among the similar components. If only the first reference label is used in the specification, the description is applicable to any one of the similar components having the same first reference label irrespective of the second reference label.

A number of variations and modifications of the disclosure may be used. It would be possible to provide for some features of the disclosure without providing others.

The present disclosure, in various aspects, embodiments, and/or configurations, includes components, methods, processes, systems and/or apparatus substantially as depicted and described herein, including various aspects, embodiments, configurations embodiments, sub combinations, and/or subsets thereof. For example, the elongated member and/or tines, barbs, flutes, etc. of the guidewire (or portions thereof) may include a roughened surface to further facilitate the elongated member's engagement of the plaque. Additionally, the roughened surface of the guidewire may be configured in a way that negates the need for additional attaching means (e.g., tines, barbs, flutes, notches, braided elements, etc.) for the guidewire to engage the plaque. Additionally, the elongated member may include a surface pattern being unroughened and roughened at various portions along its length. Those of skill in the art will understand how to make and use the disclosed aspects, embodiments, and/or configurations after understanding the present disclosure. The present disclosure, in various aspects, embodiments, and/or configurations, includes providing devices and processes in the absence of items not depicted and/or described herein or in various aspects, embodiments, and/or configurations hereof, including in the absence of such items as may have been used in previous devices or processes, e.g., for improving performance, achieving ease and/or reducing cost of implementation.

The foregoing discussion has been presented for purposes of illustration and description. The foregoing is not intended to limit the disclosure to the form or forms disclosed herein. In the foregoing Summary for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Summary, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method of removing plaque within a blood vessel, the method comprising the steps of:
 inserting a guidewire into the blood vessel, wherein the guidewire comprises:
 an elongated member over which a catheter having a lumen can be inserted; and
 a non-rotatable means coupled to the elongated member for attaching plaque within the blood vessel to the elongated member;
 attaching plaque within the blood vessel to the non-rotatable means of the guidewire by inserting the non-rotatable means into the plaque;
 inserting the catheter into the blood vessel over the guidewire;

separating at least a portion of the plaque from the blood vessel using the catheter; and removing, from the blood vessel, the guidewire and the plaque attached to the guidewire, wherein the guidewire and the plaque attached to the guidewire are removed from the blood vessel after removing the catheter from the blood vessel.

2. The method of claim 1, wherein the catheter comprises a blade for cutting the portion of the plaque from the blood vessel.

3. The method of claim 1, wherein the catheter comprises a plurality of laser emitters for ablating the portion of the plaque from the blood vessel.

4. The method of claim 1, wherein the non-rotatable means for attaching plaque within the blood vessel to the elongated member comprises a plurality of protrusions extending radially therefrom.

5. The method of claim 4, wherein the protrusions are tines.

6. The method of claim 4, wherein the protrusions are barbs.

7. The method of claim 4, wherein the plurality of protrusions extends toward a proximal end of the elongated member.

8. The method of claim 1, wherein the non-rotatable means for attaching plaque within the blood vessel to the elongated member comprises a plurality of notches within the elongated member.

9. The method of claim 1, wherein the non-rotatable means for attaching plaque within the blood vessel to the elongated member comprises an expandable braided element.

* * * * *